US006777241B1

(12) United States Patent
Naumann et al.

(10) Patent No.: US 6,777,241 B1
(45) Date of Patent: Aug. 17, 2004

(54) METHOD FOR DIAGNOSING TSE-INDUCED CHANGES IN TISSUES USING INFRARED SPECTROSCOPY

(75) Inventors: Dieter Naumann, Berlin (DE); Janina Kneipp, Berlin (DE); Elizabeth Baldauf, Dallgow (DE); Peter Lasch, Berlin (DE); Michael Beekes, Dallgow (DE)

(73) Assignee: Robert-Koch-Institut, Berlin (DE)

( * ) Notice: Subject to any disclaimer, the term of this patent is extended or adjusted under 35 U.S.C. 154(b) by 0 days.

(21) Appl. No.: 10/009,226

(22) PCT Filed: Mar. 5, 2000

(86) PCT No.: PCT/DE00/01404

§ 371 (c)(1),
(2), (4) Date: Mar. 6, 2002

(87) PCT Pub. No.: WO00/72007

PCT Pub. Date: Nov. 30, 2000

(30) Foreign Application Priority Data

May 20, 1999 (DE) .......................................... 199 23 811

(51) Int. Cl.[7] ............................................... G01N 33/00

(52) U.S. Cl. ........................ 436/86; 436/63; 436/164; 436/811

(58) Field of Search ........................... 436/86, 63, 164, 436/811; 435/41, 70.1, 70.3

(56) References Cited

U.S. PATENT DOCUMENTS

| 5,038,039 | A |  | 8/1991 | Wong et al. ................. 250/339 |
| 5,168,162 | A |  | 12/1992 | Oong et al. .................. 250/339 |
| 5,734,587 | A |  | 3/1998 | Backhaus et al. ........... 364/498 |
| 6,399,314 | B1 | * | 6/2002 | Krishnamurthy ............ 435/7.1 |

OTHER PUBLICATIONS

Choo et al. "Infrared spectra of human central nervous system tissue: diagnosis of Alzheimer's disease by multivariate analyses", Biospectroscpy, 1995, v. 1, No. 2, pp. 141–148, Abstract.*

Budinova et al. "Utilization of infrared spectroscopy in the study of human tissues", Chemicke Listy, 1996, v. 90, No. 7, pp. 433 445, Abstract.*

Caughey et al., "Secondary Structure Analysis of the Scrapic–Associated Protein PrP 27–30 in Water by Infrared Spectroscopy." Biochemistry, vol. 30, No. 31, pp. 7672–7680, May 1991.

Goodacre et al., "Rapid Identification of Streptococcus and Enterococcus Species Using Diffuse Reflectance–Absorbance Fourier Transform Infrared Spectroscopy and Artifical Neural Networks," FEMS Microbiology Letters, vol. 140, pp. 233–239, 1996.

Kneipp et al., "Detection of Pathological Molecular Alterations in Scrapie–Infected Hamster Brain by Fourier Transform Infrared (FT–IR) Spectroscopy," Biochimica et Biophysica Acta, vol. 1501, pp. 189–199, 2000.

Naumann, "Infrared and NIR Raman Spectroscopy in Medical Microbiology," SPIE, vol. 3257, pp. 245–255.

Diem et al., "Infrared Spectroscopy of Cells and Tissues: Shinning Light onto a Novel Subject," Applied Spectroscopy, vol. 53, No. 4, pp. 148A–161A, 1999.

(List continued on next page.)

Primary Examiner—Jill Warden
Assistant Examiner—Yelena G. Gakh
(74) Attorney, Agent, or Firm—Webb Ziesenheim Logsdon Orkin & Hanson, P.C.

(57) ABSTRACT

A method for diagnosing TSE-induced pathologic changes in tissues including the steps of: (a) directing infrared radiation to a tissue sample with pathologic changes caused by TSE, recording its spectral characteristics after irradiation and (b) comparing and classifying the infrared spectra thus obtained with a reference database containing infrared spectra of TSE-infected tissues and non-infected tissues.

19 Claims, 5 Drawing Sheets

OTHER PUBLICATIONS

Helm et al., "Elaboration of a Procedure for Identification of Bacteria Using Fourier–Transform IR Spectra Libraries: A Stepwise Correlation Approach," *J. of Micro. Methods*, vol. 14, pp. 127–142, 1991.

Helm et al., "Classification and Identification of Bacteria by Fourier–Transform Infrared Spectroscopy," *Journal of General Microbiology*, vol. 137, pp. 69–79, 1991.

Schmerr et al., "A Diagnostic Test for Scrapie–Infected sheep Using a Capillary Electrophoresis Immunoassay With Fluorescent–Labeled Peptides," *Electrophoresis*, vol. 19, pp. 409–414, 1998.

Zerr et al., "Protein 14–3–3," *The New England Journal of Medicine*, p. 874, 1997.

Zerr et al., "Detection of 14–3–3 Protein in the Cerebrospinal Fluid Supports the Diagnosis of Creutzfeldt–Jakob Disease," *American Neurological Association*, vol. 43, No. 1, pp. 32–40, 1998.

Otto et al., "S–100 Protein Concentration in the Cerebrospinal Fluid of Patients with Creutzfeldt–Jakob Disease," *J. Neurol.*, vol. 244, pp. 566–570, 1997.

Otto et al., "Diagnosis of Creutzfeldz–Jakob Disease by Measurement of S100 Protein in Serum: Prospective Case–Control Study," *Brit. Med. Journal*, vol. 316, pp. 577–582, 1998.

Zerr et al., "Cerebrospinal Fluid Concentration of Neuron–Specific Enolase in Diagnosis of Creutz–Jakob Disease," *The Lance*, vol. 345, pp. 1609–1610, 1995.

Otto et al., "Elevated Levels of Serum S100 Beta Protein in Scrapie Hamsters," *Journals of Neuro Virology*, vol. 4, pp. 572–573, 1998.

Safar et al., "Eight Prion Have $PrP^{Sc}$ Molecules with Different Conformations," *Nature Medicine*, vol. 4, No. 10, pp. 1157–1165, 1998.

Lasch et al., "FT–IR Microspectroscopic Imaging of Human Carcinoma Thin Sections Based on Pattern Recognition Techniques," *Cellular and Molecular Biology*, vol. 44, No. 1, pp. 189–202, 1998.

Lasch et al., "Imaging of Human Colon Carcinoma Thin Sections by FT–IR Microspectrometry," *SPEC*, vol. 3257, pp. 187–198, 1998.

Choo et al., "In Situ Characterization of β–Amyloid in Alzheimer's Diseased Tissue by Synchrotron Pourier Transform Infrared Microspectroscopy," *Biophysical Journal*, vol. 71, pp. 1672–1679, 1996.

\* cited by examiner

METHOD FOR DIAGNOSING TSE-INDUCED CHANGES IN TISSUES USING INFRARED SPECTROSCOPY

A method for diagnosing TSE-induced changes in tissues using infrared spectroscopy.

BACKGROUND OF THE INVENTION

1) Field of the Invention

This invention relates to a method for fast detection of pathologic changes induced by transmissible spongiform encephalopathies (TSE) in animal or human tissue using infrared spectroscopy (IR spectroscopy).

2) Brief Description of the Prior Art

Transmissible spongiform encephalopathies are communicable neurodegenerative diseases of the central nervous system (CNS) that may affect many mammals and humans. TSE is used as a cover term here that refers to the various forms of this disease as they occur in the various species. In addition to scrapie (trotting disease), the disease that originated in sheep but can be transmitted to hamsters and mice, five other types of TSE have become known as yet: Bovine spongiform encephalopathy (BSE) in cattle, chronic wasting disease (CWD) in some American deer and elk, transmissible mink encephalopathy (TME) in mink, feline spongiform encephalopathy (FSE) in cats, and a spongiform encephalopathy in antelopes. Four types of TSE are distinguished in humans: Creutzfeldt-Jakob disease (CJD), Gerstmann-Sträussler-Scheinker syndrome (GSS), fatal familial insomnia (FFI), and kuru.

TSE can definitely be diagnosed based on a) histological proof of characteristic spongiform changes in the brain tissue accompanied by gliosis, b) immunological proof of deposits of the pathologic prion protein (PrP) using a,Western blot test, histo-blot test, and immunohistochemistry, c) proof of scrapie-associated (PrP) fibrils (SAF) using an electron microscope, and d) proof of the infectious TSE agent using transmission experiments in animals.

Clinical symptoms and chemical laboratory findings of increased concentrations of specific proteins in cerebrospinal fluid and/or serum [Protein 14-3-3 (Zerr et al. (1997) *N. Engl. J. Med.* 336: 874; Zerr et al. (1998) *Ann. Neurol.* 43: 32–40.), Protein S100 (Otto et al. (1997) *J. Neurol.* 244: 566–570; Otto et al. (1998) *Brit. Med. J.* 316: S77S82; Otto et al. (1998) *J. Neurovirol.* 4: 572–573) as well as neuron-specific enolase (Zerr et al. (1995) Lancet 345: 1609–1610)] in animals and humans can only give rise to a tentative diagnosis. The same applies to changes visible in EEGs or MR tomograms that occur in conjunction with human TSE.

Development and improvement of detection procedures for TSE serve, inter alia, the following purposes.

a) Improving differential diagnostics of human TSEs. These diseases can only be diagnosed with any certainty by a post mortem or cerebral biopsy.

b) Detection of TSE contamination in blood, organs, and tissue and in products of human or animal origin produced from these.

c) Identification of blood, organ, and tissue donors infected with human TSE.

d) Detection of preclinical or clinical stages of TSE infection in farm animals (e.g. cattle and sheep) at the slaughterhouse or farm.

To be able to diagnose TSE diseases in farm animals is important because these diseases may be transmitted through eating the meat of diseased animals. It is suspected, for example, that the consumption of BSE-contaminated beef can cause a new variant of CJD in humans (nvCJD). Some states are currently introducing official monitoring of contamination levels in cattle populations to protect consumers and contain the spread of the epidemic. It is envisaged to carry out routine checks at slaughterhouses to establish whether the carcasses can be used.

Various test systems are being developed to provide sensitive and fast screening of large sample populations for pathologic prion protein and thus to provide diagnostics for large-scale production. These include a capillary electrophoresis immunoassay using fluorescence-labeled peptides (Schmerr & Jenny (1998) *Electrophoresis* 19: 409–419) and an immunological detection system using fluorescent lanthanide chelates called Delfia (Safar et, al. (1998) Nature Medicine 4. 1157–1165).

Only one diagnostic method is currently available to identify TSE-infected farm animals that is suitable for large-scale application. It is restricted to use at slaughterhouses and, according to the developer's statements, can detect BSE in cattle up to half a year before clinical symptoms occur (see the manufacturer's information on the Internet at http://www.prionics.ch).

In this method developed by Swiss-based Prionics AG, a tissue sample obtained from the medulla oblongata of slaughtered cattle is homogenized and treated with proteinase K enzyme. The pathologic prion protein that may remain after this treatment is labeled with the 6H4 monoclonal antibody (manufactured by Prionics) and then stained using the Western blot method. The manufacturer states that it takes up to 12 hours from taking the sample to getting a final result using this method. It is the problem of this invention to develop a method that provides fast, reliable and cost-efficient detection of TSE-induced tissue changes. The method according to the invention is to work efficiently in the routine operations of a slaughterhouse.

It is an object of this invention to provide a method for detecting TSE-induced pathologic changes in tissues. Said changes may be caused by scrapie, BSE, or any other of the TSE diseases. This objective is achieved by the present invention in the following steps: (a) directing infrared radiation onto a tissue sample and recording the spectral characteristics after interaction with the sample; (b) comparing the infrared spectrum thus obtained against a reference database containing infrared spectra of TSE-infected tissues and non-infected tissues; and (c) classifying the infrared spectrum as a spectrum obtained from TSE-infected or non-infected tissues.

DETAILED DESCRIPTION OF THE INVENTION

The method used in this invention is mainly based upon measurements of infrared spectra of pathologically changed tissue. It has been known from a number of publications and patent applications that disease-specific changes may be reflected in the infrared spectrum of tissues (U.S. Pat. No. 5,168,162 (Wong & Rigas; U.S. Pat. No. 5,038,039; Wong, Rigas; Lasch & Naumann (1998) *Cell. Mol. Biol.* 44:189–202; Lasch et al. (1998) *Proc. SPIE* 3257: 187–198; Choo et. al. (1996) *Biophys. J.* 71: 1672–1679). However, no data have been published on infrared spectroscopy performed on TSE tissue samples.

The experimental data this patent description is based on was developed using CNS samples of scrapie-infected hamsters as a model system. It was found in this hamster model that characteristic changes in the infrared spectrum of CNS tissue samples occurred after the animals were infected with scrapie. These changes were identified using the method according to the invention, i.e. by comparing respective samples obtained from non-infected healthy animals. In principle, this method can be used for the diagnosis of any clinical picture of the TSE group of diseases. According to the method of the invention, TSE diagnosis using infrared spectrography requires comparing spectra of the tissue to be examined with spectra of tissues of known origin for reference. Practical application of this method therefore requires the existence of a validated reference database of IR spectra obtained from healthy and pathologic tissue samples. This reference database has to be created just once to perform a standardized diagnostic method.

Matching spectra obtained from unknown samples with the reference database can be performed using methods of computeraided pattern recognition such as multivariate statistics, artificial neuronal networks, genetic algorithms, etc.

The spectra are obtained by directing infrared light onto the samples and recording the spectral characteristics of the emerging radiation, i.e. after the light has interacted with the tissue. Use of microspectrometric techniques is advantageous when minimization of sample sizes is desired. When an infrared microscope is used, spectral data can be obtained from thin slices of tissue in positional resolution, which makes the method considerably more specific and sensitive. In future improvements, an infrared optical waveguide could be used as an endoscope and facilitate TSE diagnosis directly in the infected organism.

Figure 1:
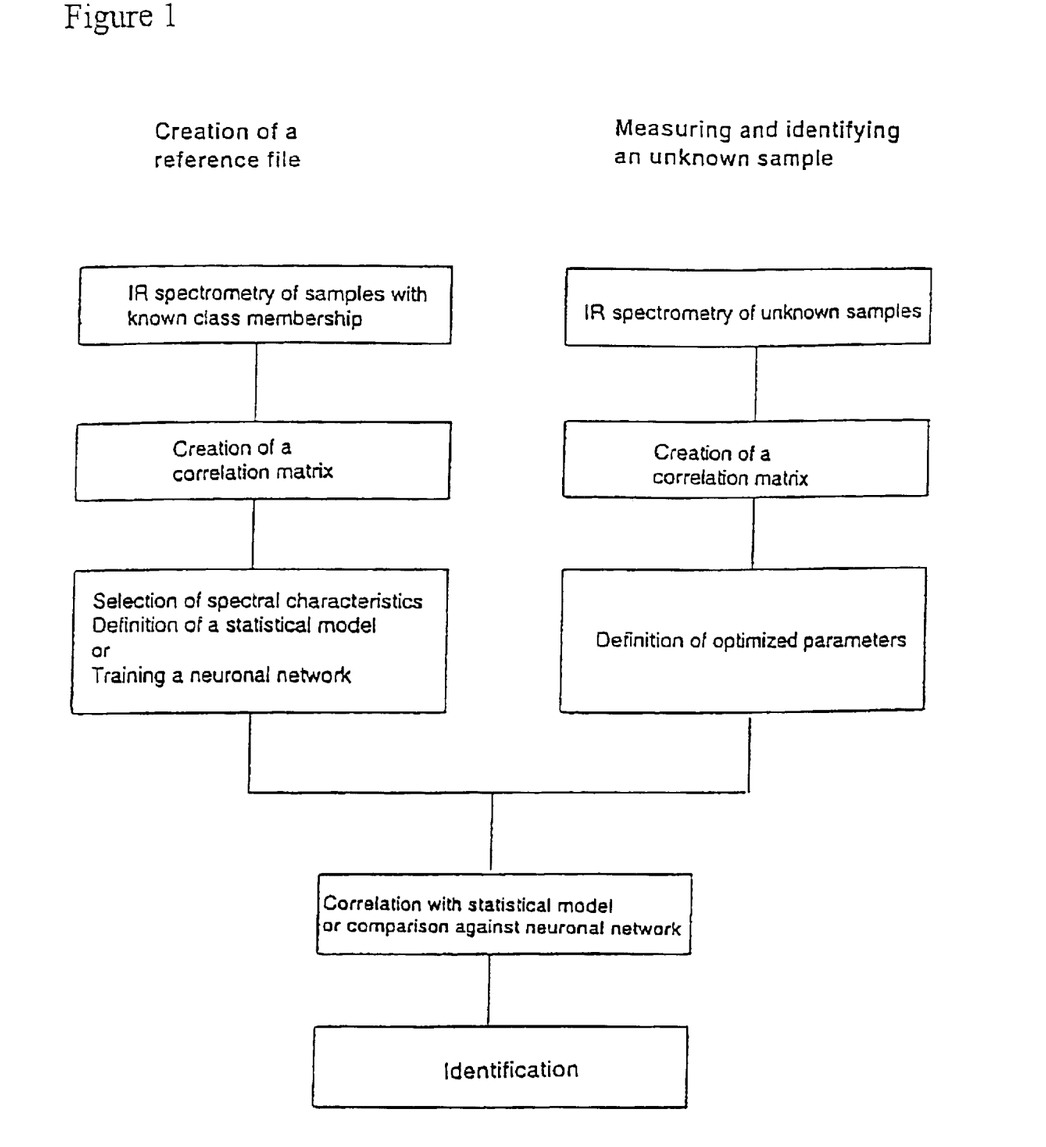
FIG. 1 is a flowchart of the method according to the present invention.

A typical flowchart of the method is shown in FIG. 1. The new method of detecting TSE-induced changes in tissue enables users to make statements within one minute from obtaining the sample. This makes it superior to immunological detection of the prion protein and immunohistological diagnosis, as these provide results after up to 12 hours only. So virtually no intermediate storage of the carcasses is required to wait for test results when the method according to the invention is used during routine operation. Fastness of this diagnostic method represents an economic advantage as compared to known methods because it minimizes the storage time of the carcasses and thus space and energy costs required for refrigerating them. In addition, the meat is fresher at the time of final consumption.

This method can easily be integrated into a routine process as the steps of recording, processing, and classifying the spectrum are fully computer-controlled and easily automated. Just a few staff members are required for the relatively simple process of sample preparation, but unlike other methods, pretreatment of the samples does not require a major effort (such as enrichment of the prion protein by proteinase K digestion) or staining thin slices of tissue (by immunohistological methods).

The method according to the invention can be performed without involving highly specialized professionals (such as histologists) as the IR spectra are classified using generally known methods of computer-aided pattern recognition that are optimized for the purposes of TSE diagnosis. As the spectra are evaluated according to strict mathematical criteria, diagnosis is highly reliable, does not require inference from experience, thus bypassing human misjudgment.

The method of the invention has an economically reasonable design due to its moderate staffing requirements and virtually no material costs during operation.

The advantage of the method according to the invention in its specific IR microscopy embodiment for analyzing thin slices of tissue in positional resolution is that it combines structural information in spectral resolution with the high positional resolution obtained from it. Involvement of individual neurons in the pathogenesis can be recorded and studied using the mapping an IR microscope can provide. The very high diagnostic sensitivity of the method results from the fact that characteristics of diseased and healthy cells are practically not averaged, which is bound to happen with methods that do not offer mapping functionality. This specific embodiment of the method still required relatively much time for data collection, which may take from 1 to 6 hours depending on the size of the tissue area under review and the positional resolution. However, it should be widely used in scientific and clinical studies of the pathogenic mechanisms of TSE which have not yet been understood. In the future, this embodiment will be combined with so-called array infrared detectors that are being developed by various manufacturers and will be capable of measuring IR spectra of complete thin slice areas in positional resolution and in a very short time, making this method eventually suitable for fast routine diagnosis.

The method of the invention first requires taking post mortem tissue samples from the organism. Samples may be taken from animal and human organisms.

The method is suitable for detecting each of the special clinical forms that are covered by the term 'transmissible spongiform encephalopathy' (TSE), such as BSE, scrapie, or CJD.

All organs that show TSE-induced pathologic changes can be used as sites for collecting tissue samples. As far as we know today, affected organs are the central nervous system, the peripheral nervous system, organs of the lymphatic system, the digestive system, the endocrine system, the cardiovascular system, and the respiratory system. Preferred collection sites are the central nervous system and the peripheral nervous system, the medulla oblongata and the Varolian pons being particularly advantageous. The tissue sample is prepared depending on the specific way the method is carried out.

Small pieces of tissue are collected for analyzing fully hydrated tissue samples. The native samples are placed into commercial IR cuvets. Alternatively, a homogenizate of the tissue material in $H_2O$ is produced, and aliquots are placed in IR cuvets. In a variation of the method, aliquots of this suspension are dried up as transparent films on IR-transmitting sample holders; the drying process is accelerated by reduced pressure (Helm et al. (1991) *J. Gen. Microbiol.* 137:69–79).

Cryostat sections are made for carrying out the method in an IR microscopy measuring arrangement for collecting specific locally mapped data. These are evenly applied to IR transparent microscopic slides. The method does not require any fixing of the thin slice of tissue. The samples are stored at a dry place at room temperature until they are measured.

In another embodiment that uses infrared waveguides, the method can be applied in vivo by introducing the waveguide into the tissue using minimal invasion technique and directly collecting the infrared spectrum from there. This embodiment requires an improvement of infrared waveguide technology to become practicable as currently available waveguides still have a too low spectral sensitivity, are too inflexible and too big. Materials suitable for cuvets or sample holders/slides for the preparation variants described above are all water-insoluble optical materials conventionally used in IR spectroscopy, while $CaF_2$ and $BaF_2$ have proven particularly useful.

The amount of substance required for IR spectra and their superficial extent can be very small. Depending on the conditions set (such as spectroscopy with or without beam focusing or using an IR microscope), sample sizes in the $\mu$g to ng ranges can be used. The diameters of the irradiated sample areas vary between 1–3 mm and 10–30 $\mu$m. The lower limit is about the size of one or a few cells (e.g. neurons).

According to the method of the invention, the infrared spectra of tissue samples that were prepared in the way described are measured. The spectra are preferably taken using a Fourier transform infrared spectrometer which has a number of known advantages as compared to conventional disperse equipment, including fast data collection and higher sensitivity. It would generally be possible to use a conventional disperse IR spectrometer but this would slow the method down. In principle, each of the generally known IR spectrometry setups (such as transmission/absorption, diminished total, direct, or diffuse reflection) can be used to measure the spectra. Transmission/absorption spectroscopy has proven particularly useful.

The infrared spectrum is typically taken in the midinfrared spectral region, i.e. between 500 and 4000 $cm^{-1}$. Narrower spectral regions even in near infrared range from 4000 to 10000 $cm^{-1}$ can also provide successful diagnosis if the user made sure that the spectra of infected and healthy tissue samples show characteristic variance in the spectral region recorded. It was found, in particular, that marked spectral differences between TSE-infected and non-infected tissues were detected in the range from 1000 to 1300 $cm^{-1}$, and that this range is particularly suited for diagnosis.

One or several suitable spectral regions can be selected by visual inspection of spectra (selecting the ranges that show the strongest and most characteristic changes as compared to the control group) or by a generally known multivariate method for selecting spectral characteristics.

The physical parameters such as spectral resolution or number of averaged spectra, etc. can be varied within the typical ranges in IR spectroscopy without having any critical practical influence on the success of classification or diagnosis. When determining the parameters for obtaining the spectra and preparing the sample, identical parameters have to be selected for all measurements including control measurements of tissue samples from non-infected animals.

Conditioning of the spectra has proven advantageous no matter which mathematical-statistical method was chosen for spectrum classification. The generally known methods that can be used here include calculation of the first or second derivation, deconvolution, or other methods to increase spectral contrast, to facilitate band recognition, and to minimize any baseline problems that may occur. When sample populations are large, upfront data reduction using methods of multivariate statistics such as factor analysis has proven helpful.

The method requires one-time creation of a database of reference spectra. Spectra of samples from TSE-infected organisms and from non-infected individuals are measured. Samples are prepared and spectra taken in the same way as with unknown samples. It is important that all parameters for reference and sample measurements are identical.

The spectrum of the sample to be examined is compared with the spectra stored in the reference database. The spectrum is preferably classified using a method of pattern recognition such as algorithms of multivariate statistics, artificial neuronal networks, or genetic algorithms. This step classifies a spectrum based on a two-class problem as being either healthy or TSE-infected.

When the method is carried out in positional resolution, the sample (a thin slice of tissue applied to a microscopic slide) is placed in the beam path of an infrared microscope. The spectra can be taken by transmission or reflection in the infrared spectrometric arrangement. Infrared spectra are taken from various tissue areas. Positional resolution can be determined by the increment between measuring positions. It is very advantageous to use a computer-controlled X-Y stage that facilitates automated spectral measurements according to a freely selectable grid with defined increments. Such X-Y stages are standard accessories of state-of-the-art IR microscopes.

The result of a measurement in position resolution (mapping) is a series of infrared spectra wherein each spectrum represents a pixel on a fictitious grid of the thin slice of tissue. In this way, IR data is obtained that completely covers the selected area of the thin slice of tissue. The result of a measurement in position resolution (mapping) is a series of infrared spectra wherein each spectrum represents a pixel on a fictitious grid of the thin slice of tissue. In this way, IR data is obtained that completely covers the selected area of the thin slice of tissue. Position-specific information about the expansion of TSE in the tissue is maintained by comparing each mapping record with the reference database and thus classifying it as being healthy or infected. The following examples are to illustrate the way in which CNS samples obtained from scrapie-infected hamsters can be distinguished from samples obtained from healthy control animals based on the disease-specific modifications in their infrared spectra using the method according to the invention.

EXAMPLE 1

Figure 2:
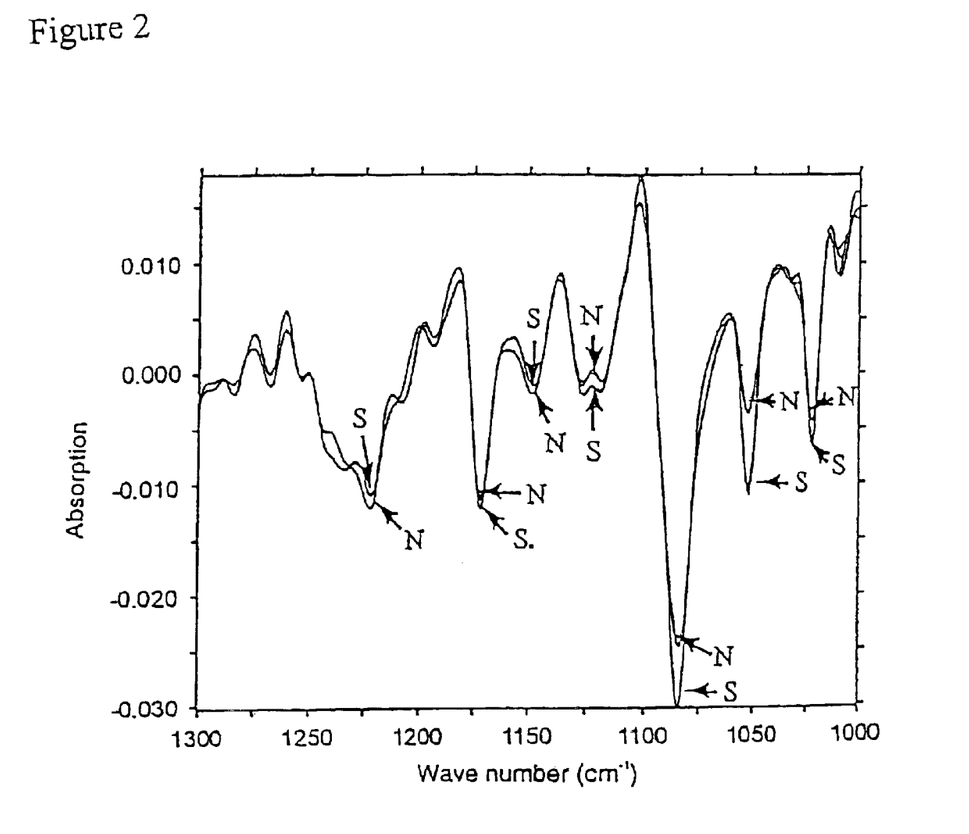
FIG. 2 is, in a first example of the present invention, a chart of two typical spectra of S- and N-tissue samples.

Adult female Syrian hamsters (*Mesocricetus auratus*) were intracerebrally and intraperitoneally infected with the 263K scrapie strain (provided by Dr. Richard Kimberlin). In the terminal stage of the disease (70 to 120 days after infection), the brains of these animals (S) and of matching noninfected control animals were removed post mortem; corresponding pairs for comparison were of similar age. Small pieces ($\mu$g-scale amounts) of the natively resected medulla oblongata and Varolian pons were put into an FTIR cuvet equipped with $CaF_2$ windows and an optical path length of 8 $\mu$m (thickness of layer). The infrared spectra of these samples were measured in transmission/absorption using an FTIR spectrometer (spectral resolution: 4 $cm^{-1}$, apodization: Happ-Genzel, number of scans: 126, zero filling: 4). Two typical spectra of S- and N-tissue samples are shown in FIG. 2 in the spectral region from 1300 to 1000 $cm^{-1}$ in which differences that can be observed are particularly prominent. The second derivations are represented for improved visualization of the bands, showing the band peaks as minima.

EXAMPLE 2

In a variation of the embodiment described in Example 1, 10 S- and 10 N-samples obtained as in Example 1 were homogenized in $H_2O$ (10 $\mu$l of $H_2O$ per mg of tissue material). Aliquots of 35 $\mu$l of the suspensions were applied to a PC-controlled multiple sample holder made of ZnSe that is also suitable for measuring microbial samples (Helm et al. (1991) *J. Gen. Microbiol.* 137:69–79; Heim et al. (1991) *J.*

Figure 3:
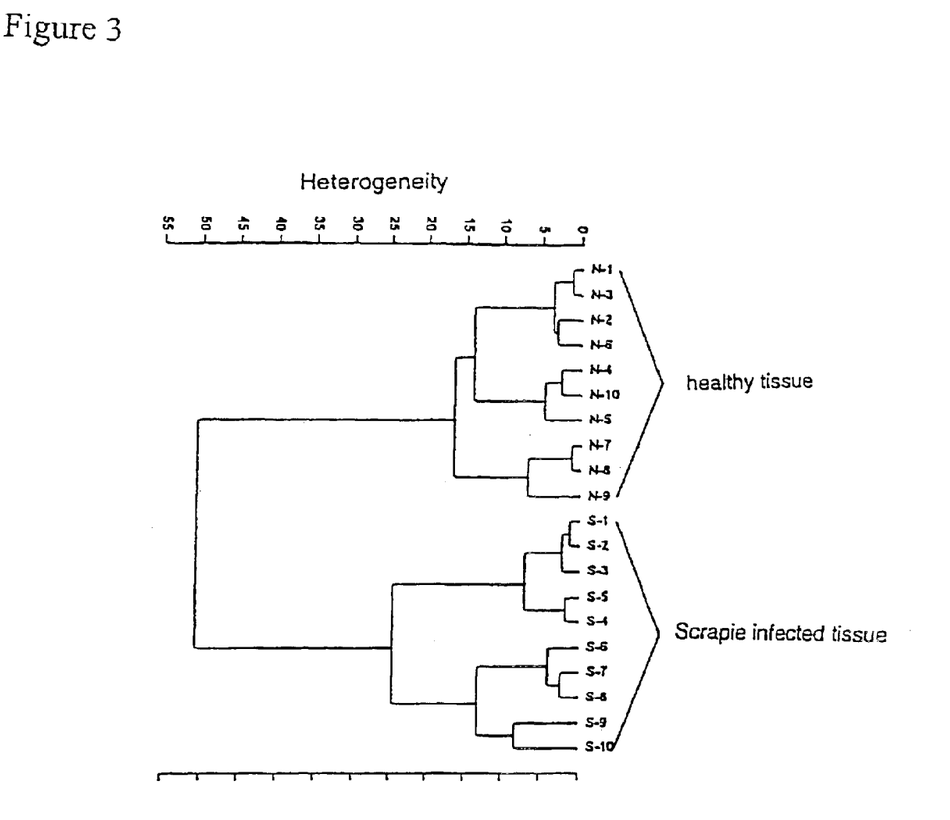
FIG. 3 is, in a second example of the present invention, a dendrogram of a specific hierarchical spectrum classification as calculated using Ward's-algorithm.

Microbiol. Meth. 14:127–142; Neumann (1998) *Proc. SPIE* 3257:245–257), and dried as described in the literature. The infrared transmission spectra of the films thus obtained were taken and classified hierarchically based on second derivations of these spectra in the spectral region from 1100 to 1000 cm$^{-1}$. FIG. 3 shows the dendrogram of this spectrum classification as calculated using Ward's algorithm. The spectra of infected animals (S-3 through S-10) could be perfectly distinguished from those of the healthy animals (N-1 through N-10).

EXAMPLE 3

Figure 4A:
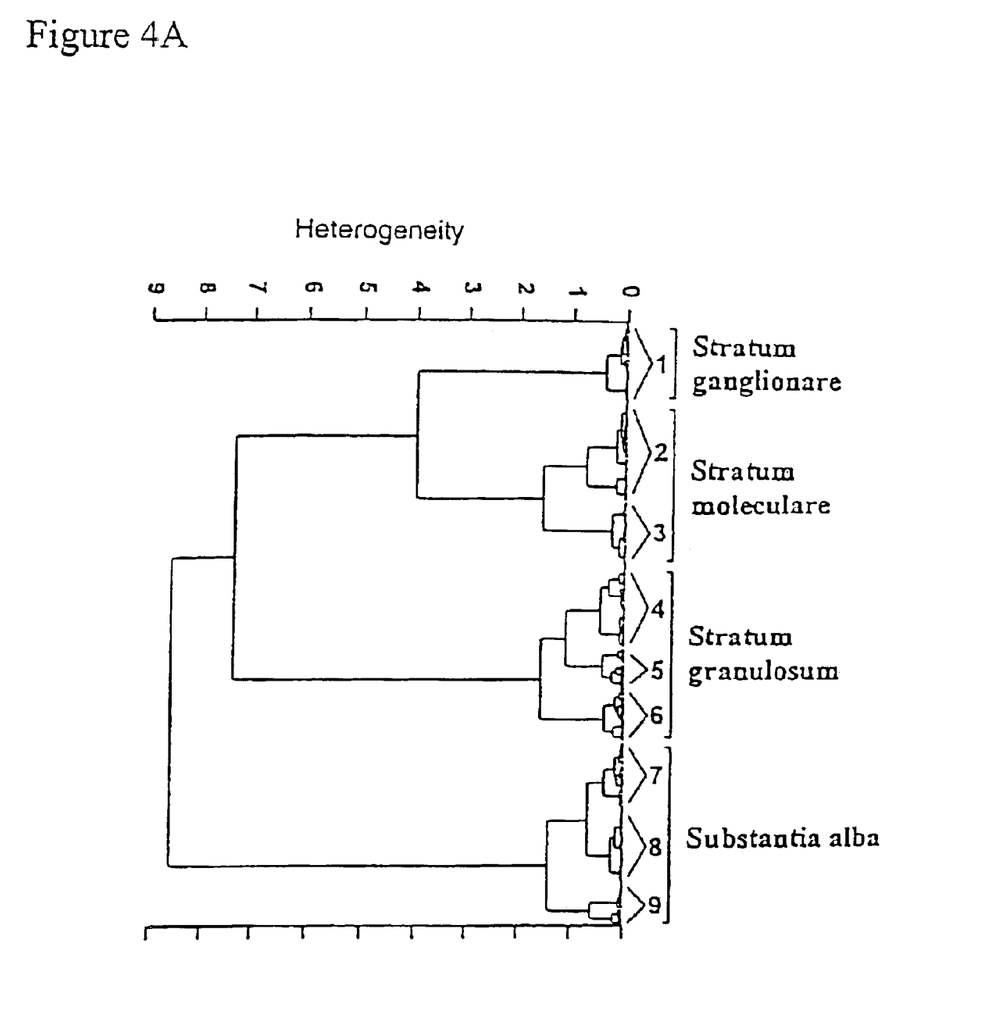
FIG. 4A is, in a third example of the present invention, a dendogram calculated after data compression using principal component analysis.
Figure 4B:
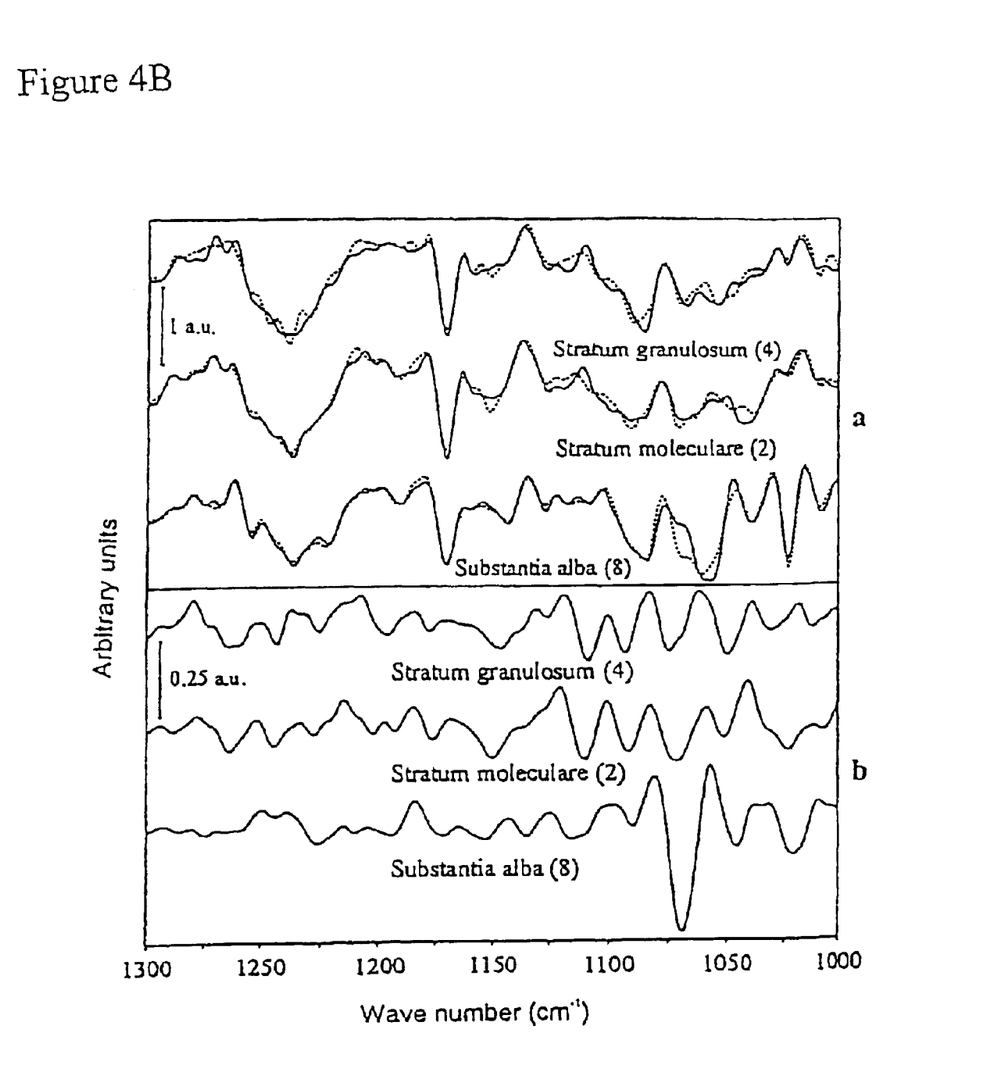
FIG. 4B, in the third example of the present invention, compares normed vector second derivations of sample spectra and differential spectra of normed vector S- and N-spectra.

In a variation of the embodiments described in Examples 1 and 2, cryostat sections were created of CNS samples obtained from N- and S-animals as described above, and measured and characterized using the generally known method of FTIR mapping (Diem et al. (1999) *Appl. Spectroscopy* 53: 148A–160A; Lasch & Neumann (1998) *Cell. Mol. Biol.* 44; 189–202; Choo et al. (1996) *Biophys. J.* 71:1672–1679) and infrared imaging (Lasch & Neumann (1998) *Cell. Mol. Biol.* 44:189–202; Lasch et al. (1998) *Proc. SPIE* 3257:187–198). Spectra were taken of 1.5 mm by 1.5 mm areas in increments of 50 μm through an aperture of 60 μm. The spectra obtained from the S- and N-samples were first separately classified in hierarchies to differentiate the typical spectra for the various brain structures. FIG. 4A shows a dendrogram that was calculated after data compression using principal component analysis based on the first three principal components between 1450 and 950 cm$^{-1}$ (ca. 500 data points). The four main classes can be assigned to the four histologically defined cerebral structures: molecular layer, ganglion cell layer, granular cell layer, and white substance matter. In addition, nine spectral classes (numbered 1 to 9) were separated that correspond to specific structures within the cerebellum. FIG. 4A only shows each third spectrum of the mapping record that contains 930 spectra for better clarity. Subsequently, the spectra of corresponding spectral classes (e.g. class 2 of the molecular layer spectra—the gray substance of the cerebellum) of the N- and S-samples were compared. The upper part of FIG. 4B (*a*) compares normed vector second derivations of sample spectra from scrapie-infected animals (dashed line) and from healthy animals (solid line). The lower part shows differential spectra of normed vector S- and N-spectra from a) for the respective tissue structures. All spectra used for this comparison are averages of spectra of a spectral class A, FIG. 4A). They are identified by the name of their cerebellar layer and the number of their spectral class. The characteristic spectral differences observed for each tissue class are suitable for reliably diagnosing the disease-associated pathogenetic process.

We claim:

1. A method for diagnosing transmissible spongiform encenhalopathies-induced (TSE-induced) pathologic changes in tissues, said changes being caused by scrapie, bovine spongiform encephalopathies (BSE, or another disease of the TSE group of diseases, comprising the steps of:
   (a) directing infrared radiation onto a tissue sample and recording the spectral characteristics after interaction with the sample;
   (b) comparing the infrared spectrum thus obtained against a reference database that contains infrared spectra of TSE-infected and non-infected tissues; and
   (c) classifying the infrared spectrum as a spectrum obtained from TSE-infected or non-infected tissues.

2. The method according to claim 1, wherein said tissue sample is collected from one of the central nervous system, the peripheral nervous system and human organs.

3. The method according to claim 2, wherein the human organs are from one of the lymphatic system, the digestive system, the endocrine system, the cardiovascular system and the respiratory system.

4. The method according to claim 2, wherein said infrared spectrum of the tissue is measured in at least one region of one of the mid-infrared range from 500 to 4000 cm$^{-1}$ and the near infrared range from 4000 to 10000 cm$^{-1}$.

5. The method according to claim 2, wherein said infrared spectrum of the tissue is measured in the spectral region from 1000 to 1300 cm$^{-1}$ of the mid-infrared range.

6. The method according to claim 1, wherein said infrared spectrum of the tissue is measured in at least one region of one of the mid-infrared range from 500 to 4000 cm$^{-1}$ and the near infrared range from 4000 to 10000 cm$^{-1}$.

7. The method according to claim 2, wherein said infrared radiation interacts with said sample, and the characteristically altered radiation is detected in one of a transmission/absorption, attenuated total reflection, direct reflection measuring setup, diffuse reflection measuring setup, and by using IR waveguides.

8. The method according to claim 6, wherein said infrared radiation interacts with said sample, and the characteristically altered radiation is detected in one of a transmission/absorption, attenuated total reflection, direct reflection measuring setup, diffuse reflection measuring setup, and by using IR waveguides.

9. The method according to claim 1, wherein said infrared spectrum of the tissue is measured in the spectral region from 1000 to 1300 cm$^{-1}$ of the mid-infrared range.

10. The method according to claim 1, wherein said infrared radiation interacts with said sample, and the characteristically altered radiation is detected in one of a transmission/absorption, attenuated total reflection, direct reflection measuring setup, diffuse reflection measuring setup, and by using IR waveguides.

11. The method according to claim 1, wherein said infrared spectrum of the sample to be examined is compared against the reference database using at least one method of pattern recognition, and that the spectral regions said comparison is based on are determined using methods for extracting optimum spectral characteristics.

12. The method according to claim 11, wherein the at least one pattern recognition method uses algorithms of one of multivariate statistics and artificial neuronal networks.

13. The method according to claim 11, wherein the extracting optimum spectral characteristic method uses genetic algorithms.

14. The method according to claim 1, wherein said infrared spectrum is measured on a thin slice of tissue using an IR microscope set up for one of transmission and direct reflection spectrometry.

15. The method according to claim 14, wherein said infrared spectra are measured in positional resolution.

16. The method according to claim 14, wherein each mapped infrared spectrum is compared against the reference database, thereby providing localized information on the spread of the disease in the tissue.

17. The method according to claim 14, wherein said reference database contains reference spectra of TSE-infected tissues and non-infected tissues of all structures that can be distinguished in the tissue section using infrared spectroscopy.

18. The method according to claim 14, wherein said infrared spectra are mapped to the tissue site where the infrared beam is transmitted through the sample.

19. The method according to claim 18, wherein each mapped infrared spectrum is compared against the reference database, thereby providing localized information on the spread of the disease in the tissue.

* * * * *

UNITED STATES PATENT AND TRADEMARK OFFICE
CERTIFICATE OF CORRECTION

PATENT NO. : 6,777,241 B1
DATED : August 17, 2005
INVENTOR(S) : Naumann et al.

It is certified that error appears in the above-identified patent and that said Letters Patent is hereby corrected as shown below:

Title page,
Item [22], PCT Filed, "Mar. 5, 2000" should read -- May 3, 2000 --.
Item [75], Inventors, "Elizabeth Baldauf, Dallgow (DE); and Michael Beekes, Dallgow (DE)" should read -- Elizabeth Baldauf, Falkensee (DE) and Michael Beekes, Falkensee (DE) --.
Item [56], References Cited, OTHER PUBLICATIONS,
"Choo et al.," reference (first occurrence), "Biospectroscpy" should read
-- Biospectroscopy --.
"Budinova al.," reference, "433 445" should read -- 443—445 --.
"Caughey et al.," reference, "Scrapic-Associated" should read -- Scrapie-Associated --.
"Helm et al.," reference (first occurrence), "Spectra Libraries" should read -- Spectral Libraries --.
"Schmerr et al.," reference, "sheep Using" should read -- Sheep Using --.
"Otto et al.," reference (first and second occurrences), "Creutzfeldz-Jacob" should read -- Creutzfeldt-Jakob --.
"Zerr et al.," reference (third occurrence), "Creutz-Jakob" should read -- Creutzfeldt-Jakob --; and "*The Lance*" should read -- *The Lancet* --.V *Nirology*" should read
-- *Journal of Neuro Virology* --.
"Safar et al.," reference, "Eight Prion Have" should read -- Eight Prion Strains Have --.
"Lasch et al.," reference (second occurrence), "SPEC" should read -- SPIE --.
"Choo et al.," reference (second occurrence), Synchrotron Pourier" should read
-- Synchrotron Fourier --.

Column 2,
Line 36, before the paragraph beginning "It is an object of this invention", add the title
-- SUMMARY OF THE INVENTION --.

Column 7,
Line 51, "encenhalopathies" should read -- encephalopathies --.

UNITED STATES PATENT AND TRADEMARK OFFICE
CERTIFICATE OF CORRECTION

PATENT NO.   : 6,777,241 B1
DATED        : August 17, 2005
INVENTOR(S)  : Naumann et al.

It is certified that error appears in the above-identified patent and that said Letters Patent is hereby corrected as shown below:

Column 7 (cont'd),
Line 53, "encegalopathies (BSE," should read -- encephalopathies (BSE) --.

Signed and Sealed this

Twenty-third Day of August, 2005

JON W. DUDAS
*Director of the United States Patent and Trademark Office*